(12) United States Patent
Goetz et al.

(10) Patent No.: US 9,433,502 B2
(45) Date of Patent: Sep. 6, 2016

(54) APPARATUS AND SET FOR FOLDING OR UNFOLDING A MEDICAL IMPLANT AND METHOD

(75) Inventors: Wolfgang Goetz, Regensburg (DE); Hou-Sen Lim, Singapore (SG)

(73) Assignee: VENUS MEDTECH (HANGZHOU), INC., Hangzhou (CN)

( * ) Notice: Subject to any disclaimer, the term of this patent is extended or adjusted under 35 U.S.C. 154(b) by 232 days.

(21) Appl. No.: 13/512,324

(22) PCT Filed: Nov. 26, 2010

(86) PCT No.: PCT/EP2010/007183
§ 371 (c)(1),
(2), (4) Date: Jul. 12, 2012

(87) PCT Pub. No.: WO2011/063972
PCT Pub. Date: Jun. 3, 2011

(65) Prior Publication Data
US 2012/0277734 A1 Nov. 1, 2012

Related U.S. Application Data

(60) Provisional application No. 61/265,367, filed on Dec. 1, 2009.

(30) Foreign Application Priority Data

Nov. 27, 2009 (DE) .......................... 10 2009 055 969

(51) Int. Cl.
*A61F 2/24* (2006.01)
*A61F 2/95* (2013.01)

(52) U.S. Cl.
CPC .............. *A61F 2/2439* (2013.01); *A61F 2/95* (2013.01); *A61F 2/2412* (2013.01); *A61F 2002/9505* (2013.01); *A61F 2002/9511* (2013.01)

(58) Field of Classification Search
CPC .............. A61F 2/95; A61F 2002/9505; A61F 2002/9511; A61F 2/2427; A61F 2/2436; A61F 2/966; A61F 2/2439
USPC ........ 606/108, 151, 153, 200, 139, 140, 141, 606/142, 143, 146, 148, 213, 232, 138; 623/1.11, 1.12, 1.23, 2.11, 23.72
See application file for complete search history.

(56) References Cited

U.S. PATENT DOCUMENTS 5,387,235 A * 2/1995 Chuter .................... 623/1.11
5,480,423 A * 1/1996 Ravenscroft et al. ....... 623/1.11
(Continued)

FOREIGN PATENT DOCUMENTS

JP 2000-325484 A 11/2000
JP 2003-502107 A 1/2003
(Continued)

*Primary Examiner* — Ryan J Severson
*Assistant Examiner* — Christian Knauss
(74) *Attorney, Agent, or Firm* — Hamre, Schumann, Mueller & Larson, P.C.

(57) ABSTRACT

The present invention relates to an apparatus (100) for folding or unfolding at least one medical implant (300) by using at least one tension thread (11, 11'), wherein the apparatus (100) includes a shaft (1) including a reception area for receiving the implant (300), a tensioning device (19) for altering a shape of the foldable and/or unfoldable implant (300) by means of the tension thread (11, 11'), and a separation device for separating the tension thread (11, 11') from the implant (300) and/or for cutting through the tension thread (11, 11'). The invention further relates to a set and a method.

15 Claims, 10 Drawing Sheets

(56) References Cited

U.S. PATENT DOCUMENTS

| | | | |
|---|---|---|---|
| 5,571,086 A * | 11/1996 | Kaplan et al. | 604/96.01 |
| 5,653,748 A * | 8/1997 | Strecker | 623/1.11 |
| 5,693,084 A * | 12/1997 | Chuter | 623/1.35 |
| 5,755,777 A * | 5/1998 | Chuter | 623/1.11 |
| 5,800,521 A * | 9/1998 | Orth | 623/1.23 |
| 5,941,908 A * | 8/1999 | Goldsteen et al. | 623/1.23 |
| 5,957,949 A * | 9/1999 | Leonhardt et al. | 623/1.24 |
| 6,183,504 B1 * | 2/2001 | Inoue | 623/1.11 |
| 6,245,097 B1 * | 6/2001 | Inoue | 623/1.11 |
| 6,287,315 B1 * | 9/2001 | Wijeratne et al. | 606/108 |
| RE38,091 E * | 4/2003 | Strecker | 623/1.12 |
| 6,599,311 B1 | 7/2003 | Biggs et al. | |
| 6,733,509 B2 * | 5/2004 | Nobles et al. | 606/138 |
| 6,764,503 B1 * | 7/2004 | Ishimaru | 623/1.11 |
| 6,767,358 B2 * | 7/2004 | Leonhardt et al. | 623/1.13 |
| 6,852,116 B2 * | 2/2005 | Leonhardt et al. | 606/108 |
| 7,611,528 B2 * | 11/2009 | Goodson et al. | 623/1.11 |
| 7,837,727 B2 * | 11/2010 | Goetz et al. | 623/2.18 |
| 7,909,863 B2 * | 3/2011 | Hartley et al. | 623/1.13 |
| 7,993,383 B2 * | 8/2011 | Hartley et al. | 623/1.11 |
| 8,523,932 B2 * | 9/2013 | Roeder et al. | 623/1.11 |
| 2002/0087178 A1 * | 7/2002 | Nobles et al. | 606/167 |
| 2002/0099431 A1 * | 7/2002 | Armstrong et al. | 623/1.11 |
| 2002/0099432 A1 * | 7/2002 | Yee | 623/1.11 |
| 2002/0183825 A1 * | 12/2002 | Solem | 623/1.11 |
| 2003/0060837 A1 * | 3/2003 | Solem | 606/153 |
| 2003/0195607 A1 * | 10/2003 | Trout et al. | 623/1.13 |
| 2003/0225445 A1 * | 12/2003 | Derus et al. | 623/1.11 |
| 2003/0233140 A1 * | 12/2003 | Hartley et al. | 623/1.11 |
| 2004/0049256 A1 * | 3/2004 | Yee | 623/1.12 |
| 2005/0085888 A1 * | 4/2005 | Andreas et al. | 623/1.11 |
| 2005/0090834 A1 * | 4/2005 | Chiang et al. | 606/108 |
| 2005/0096721 A1 * | 5/2005 | Mangin et al. | 623/1.11 |
| 2005/0119722 A1 * | 6/2005 | Styrc et al. | 623/1.12 |
| 2006/0190071 A1 * | 8/2006 | Armstrong et al. | 623/1.12 |
| 2007/0005081 A1 | 1/2007 | Findlay, III et al. | |
| 2007/0083255 A1 * | 4/2007 | Chiang et al. | 623/1.11 |
| 2007/0203559 A1 * | 8/2007 | Freudenthal et al. | 623/1.3 |
| 2007/0293929 A1 * | 12/2007 | Aoba et al. | 623/1.11 |
| 2008/0140178 A1 * | 6/2008 | Rasmussen et al. | 623/1.11 |
| 2008/0262592 A1 * | 10/2008 | Jordan et al. | 623/1.11 |
| 2009/0005863 A1 | 1/2009 | Goetz et al. | |
| 2009/0024137 A1 * | 1/2009 | Chuter et al. | 606/108 |
| 2009/0099640 A1 | 4/2009 | Weng | |
| 2009/0204196 A1 * | 8/2009 | Weber | 623/1.2 |
| 2009/0312829 A1 * | 12/2009 | Aoba et al. | 623/1.11 |
| 2011/0040366 A1 | 2/2011 | Goetz et al. | |

FOREIGN PATENT DOCUMENTS

| | | |
|---|---|---|
| JP | 2006-520240 A | 9/2006 |
| WO | 00/78248 A1 | 12/2000 |
| WO | 2005/037361 A2 | 4/2005 |
| WO | 2009/109348 A1 | 9/2009 |

* cited by examiner

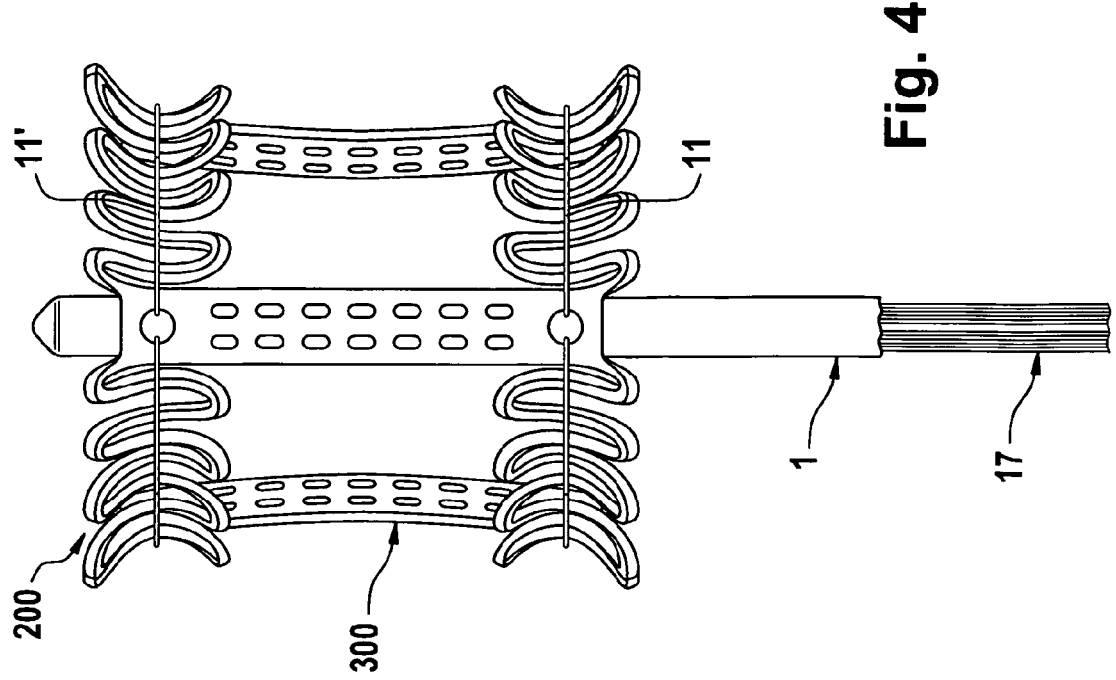
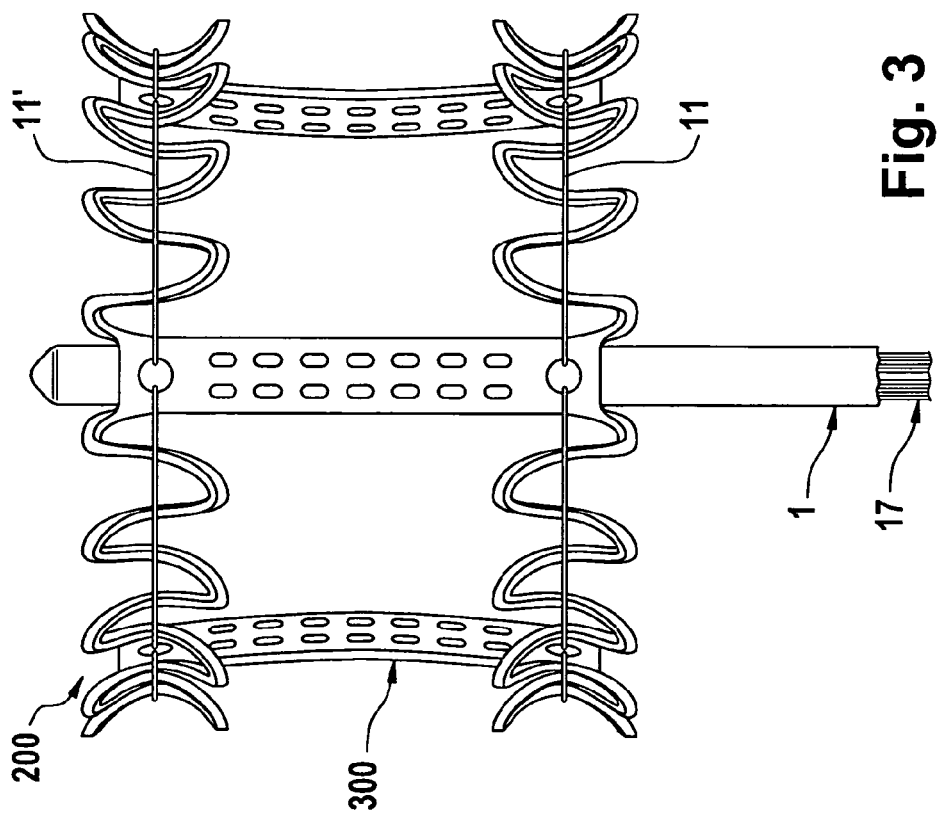

APPARATUS AND SET FOR FOLDING OR UNFOLDING A MEDICAL IMPLANT AND METHOD

CROSS-REFERENCE TO RELATED APPLICATIONS

This application is filed under 35 U.S.C. §371 as a U.S. national phase application of PCT/EP2010/007183, having an international filing date of Nov. 26, 2010, which claims priority to German Patent Application No. 10 2009 055 969.8, filed Nov. 27, 2009, and U.S. provisional patent application No. 61/265,367, filed on Dec. 1, 2009, the contents of which are incorporated herein by reference.

The present invention relates to an apparatus for folding or unfolding an implant, and to a set. The invention further relates to a method.

From practice, implants are known, which can be folded or unfolded by using one or several threads or filaments transferring tension to the implant. Furthermore, corresponding apparatuses for folding and unfolding are known from practice.

One object of the present invention is to suggest an apparatus for folding or unfolding a foldable and/or unfoldable implant by using a tension thread. Furthermore, the present invention provides a suitable set including such an apparatus, a method for folding and/or unfolding an implant as well as a method for cutting a tension thread.

According to the invention, an apparatus for introducing and/or folding and/or unfolding an implant by using at least one tension thread is suggested. The apparatus according to the invention includes a shaft having a reception area for receiving the implant.

The apparatus further includes at least one tensioning device for altering a shape of the foldable and/or unfoldable implant by means of the tension thread.

Additionally, the apparatus includes a separation device for separating at least one tension thread from the implant and/or for cutting the tension thread.

Advantageous embodiments and/or developments are subject of the dependent claims.

In one embodiment of the apparatus according to the present invention, altering the shape of the implant means reducing or increasing a diameter, particularly an external diameter, of the implant. Such an alteration can or cannot involve an alteration of the implant's length or any other kind of alteration.

In one embodiment of the apparatus of the present invention, folding the implant means reducing the diameter of the implant.

In certain embodiments according to the invention, unfolding should be understood as increasing the diameter of the implant.

In one embodiment, the diameter of the implant is arranged in one plane perpendicular to a main flow direction of the implant in case fluids flow through the implant after its implantation.

In one embodiment of the apparatus according to the invention, the at least one tension thread is a thread. The thread can be similar to a surgical suture thread. The thread can have the shape of a rope, a filament or of a cord. The thread can be designed as a chain having a plurality of engaging chain links.

In the following, the term thread or tension thread may also define a plurality of threads or tension threads whenever a person skilled in the art recognizes the exchangeability of the terms.

In certain embodiments, the shaft of the apparatus is rigid. In some embodiments, the shaft of the apparatus is flexible in one or more directions (i.e., in a longitudinal direction or in a direction of the width of the shaft, respectively, in both directions or in other directions). In certain embodiments, the shaft is elongatable. In some embodiments, the shaft is stiff.

In one embodiment of the apparatus according to the present invention, the implant in its implanted state is permeable for fluids in its longitudinal direction. Permeable means the fluid can flow through the implant.

In one embodiment of the apparatus according to the invention, the implant is—at least transiently or temporarily—mounted or loosely arranged on or at the reception area of the apparatus at the moment of unfolding or folding.

In one embodiment of the apparatus according to the present invention, the tensioning device includes at least one pulling device. The pulling device is arranged and/or provided in such a way that it can indirectly or directly apply a tension on the implant for altering the shape of the implant by means of the tension thread.

Alternatively or additionally, in one embodiment of the apparatus according to the present invention, the pulling device is arranged and/or provided in such a way that it can reduce a tension applied on the implant by means of the tension thread.

In one embodiment of the apparatus according to the invention, the pulling device is arranged and/or provided such that it can interact with the tension thread in order to transfer force or tension.

In one embodiment of the apparatus according to the invention, the pulling device and the tension thread are intricate with each other.

In one embodiment according to the invention, the term "intricate" is used to indicate that the tension thread is movable in at least one direction of space or in two directions of space relative to the pulling device.

According to certain embodiments of the invention, the term "movable" is to be understood as "slidable".

According to one embodiment of the present invention, the term "intricate" means that the tension thread is movably arranged relative to the pulling device like a first link of a chain is movably arranged relative to an adjacent second link of this chain to which the first link is usually connected in a chain.

In one embodiment of the invention, the term "intricate" shall indicate that the tension thread is simply crossed once with or wrapped around the pulling device or sections thereof.

In one embodiment of the invention, the transfer (or the transmittal, respectively) of force or tension between the pulling device and the tension thread is achieved by a non-form closure connection.

In one embodiment according to the invention, the transfer of force or tension between the pulling device and the tension thread is achieved by a frictional connection.

In one embodiment of the apparatus according to the present invention, the pulling device is embodied as at least one pulling thread or consists of at least one pulling thread.

In one embodiment of the apparatus according to the present invention, the tension thread and/or the pulling thread includes or constitutes at least one bundle or a plurality of threads or thread elements or consists thereof.

In one embodiment of the apparatus according to the invention, the separation device includes at least one cutting device for cutting (or cutting through) the tension thread or consists thereof.

In certain embodiments according to the present invention, the separation device it not a wire or a thread (or a multitude thereof, respectively).

In some embodiments according to the present invention, the separation device is not embodied as a lock wire or lock thread that is withdrawn from the apparatus so as to allow for removing tension threads from the apparatus after final placement of the implant.

In certain embodiments according to the present invention, the separation device does not comprise hooks and/or does not comprise rings for guiding or limiting tension strings or threads.

In some embodiments according to the present invention, the separation device is embodied and/or intended to stay with the apparatus even after termination of the implantation of the implant.

In certain embodiments according to the present invention, the separation device may not be separated from the apparatus except for cleaning or the like.

In some embodiments according to the present invention, the separation device is embodied such that it is intended to be used only within the patient's body.

In certain embodiments according to the present invention, the separation device is not intended to be used for separating the tension threads from implant from outside the patient's body.

In some embodiments according to the present invention, the separation device can not be used to separate the tension strings without the presence and/or the support of the apparatus.

In one embodiment according to the invention, the apparatus includes at least one sleeve. The sleeve can preferably be made tube-like (that is, it can have a hollow inside), like a hollow cylinder, like a ring or the like. The sleeve can be designed symmetrically or asymmetrically, both relative to its opening direction and in another direction, particularly in a direction or plane perpendicular to the opening direction or the fluid passage direction, as well.

In one embodiment of the apparatus according to the present invention, the separation device is designed as a—preferably integral—part of a sleeve aperture in one wall of the sleeve of the apparatus. The sleeve aperture connects an exterior of the sleeve with an interior of the sleeve.

The sleeve aperture is in this embodiment designed as a passage opening or a through opening. It can thus be as thick as the wall of the sleeve is in a radial direction of the apparatus.

In one embodiment of the apparatus according to the invention, the sleeve aperture includes at least one first recess. At least one tension thread can be led or guided through—or by means of—this first recess.

In one embodiment of the apparatus according to the present invention, the first recess includes a first portion or first area which includes a cutting device for cutting through the tension thread.

In certain embodiments, the cutting device is or comprises a cutting edge. In some embodiments, the cutting device is attached to the sleeve. In certain embodiments, the cutting device is integrally formed with the sleeve.

In one embodiment of the apparatus according to the invention, the first recess includes a second portion or second area which does not include a cutting device.

In one embodiment of the apparatus according to the invention, the sleeve aperture includes at least one second recess in which at least one tension thread can be led or guided, preferably in the same way as with the first recess.

In doing so, the first recess and the second recess can be separated from each other by means of a bar in such a way that at least two tension threads can be led or guided in the recesses while being spaced apart from another.

Providing a distance between the two recesses can allow the leading of one or more tension threads having been distributed to the two recesses without touching each other in the area of the recesses. Thus, the leading of several tension threads through one sleeve aperture is advantageously possible without the tension threads constricting or hindering themselves. Additionally, the separated leading of tension threads being favored by providing several recesses advantageously allows for a separate treatment or use of each single tension thread: tension threads being led through a first recess can thus advantageously be differently use or treated tension threads being led through a second recess.

In one embodiment of the apparatus according to the present invention, the bar is part of the sleeve. Hence, the bar is part of the sleeve wall and/or integrally formed therewith.

Both recesses given above can also be referred to as niches, as extensions, as indentations, as furcations, as notches and so on (this can also apply for third, fourth and several more recesses). All of these terms have in common that the recesses, niches or the like branch off a common, particularly wide, area of the sleeve aperture or are connected therewith.

In one embodiment of the apparatus according to the invention, at least the first recess (or any other recess) extends in one dimension of the apparatus (preferably in a longitudinal extension of the apparatus) differently than at least the second recess does in the same dimension of the apparatus.

In one embodiment according to the invention, the shaft of the apparatus is permeable or has a passage for fluids in its interior in at least some sections of its longitudinal direction. The shaft has a wall. The shaft includes at least one shaft aperture. The at least one shaft aperture is preferably rather arranged on a lateral area of the shaft than on the front side thereof.

In one embodiment of the present invention, the shaft of the apparatus includes a plurality of shaft apertures having been uniformly or non-uniformly distributed along one or more circumferences and/or along the longitudinal extension of the shaft.

Tension threads for folding and/or unfolding the implant can enter and/or leave the apparatus through the shaft aperture. During use of the apparatus, the sleeve is arranged in an interior or in an exterior of the shaft such that tension threads can (preferably unrestrictedly and/or directly) be led from the exterior of the apparatus into an interior of the apparatus.

In one embodiment of the apparatus according to the present invention, the tension threads can be led unrestrictedly and/or directly, that means without having to be bent or redirected, from an exterior of the apparatus into an interior of the apparatus, particularly into an interior of the sleeve and/or into an interior of the shaft.

In one embodiment of the apparatus according to the invention, the sleeve is preferably arranged in a shiftable manner.

The sleeve can preferably surround the shaft in such a way that the shaft is located inside the sleeve and the sleeve is at an outside of the shaft. The at least one tension thread can thus pass from an exterior of the sleeve through the shaft aperture into an interior of the shaft (or vice versa).

Alternatively, the sleeve can be located inside of the shaft such that the shaft is surrounding the sleeve. The at least one tension thread can thus pass from an exterior of the shaft through the shaft aperture and through the sleeve aperture into the interior of the sleeve (or vice versa).

In one embodiment of the apparatus according to the invention, the apparatus includes a pre-tensioning device which is arranged for exerting tension on the sleeve in at least one state of use.

In one embodiment of the apparatus according to the present invention, the pre-tensioning device exerts a tension on the sleeve substantially or exclusively in a longitudinal direction of the shaft In certain embodiments of the apparatus according to the present invention, the pre-tensioning device exerts a tension on the sleeve so as to twist the sleeve relative to the shaft.

In one embodiment of the invention, the pre-tensioning device is embodied as a spring, particularly as a coil spring, and/or is embodied from any suitable—preferably from elastic or flexible—material such as rubber.

In certain embodiments of the apparatus according to the present invention, the pre-tensioning device is arranged for build up or maintaining the pre-tension in a pushing manner.

In some embodiments of the apparatus according to the present invention, the pre-tensioning device is arranged for build up or maintaining the pre-tension in a pulling manner.

In one embodiment of the apparatus according to the present invention, the pre-tensioning device is arranged for maintaining the separation device and/or the cutting device and/or the sleeve in a non-separating position in which no tension thread is separated from the implant and in which no tension thread is cut through.

In one embodiment of the apparatus according to the invention, the apparatus includes a device with which the separation device and/or the cutting device and/or the sleeve is transferred into a separating position in which at least one tension thread is separated from the implant or in which at least one tension thread is cut (through).

In one embodiment according to the invention, said device which enables a transfer or transition from the non-separating position into the separating position is embodied as a pulling device as, e.g., a thread or the like. In another embodiment, said device is embodied as a pushing or twisting device.

In one embodiment, said device which enables a transfer or transition from the non-separating position into the separating position includes at least one pulling thread or pushing means or twisting means which is led from its branching off at the sleeve to an exterior of the apparatus. The end of the thread or pushing means or twisting means which is distal to or far from the sleeve can be connected to a grasping device suited for grasping the thread for the purpose of pulling or pushing or twisting it. At an exterior thereof, the apparatus can include—but does not have to include—a snapping device for releasably receiving the grasping device. The grasping device can rest on the snapping device until its use.

In one embodiment of the apparatus according to the invention, said device is arranged such that it can only be transferred from a non-separating position into the separating position by overcoming the effect of the pre-tensioning device.

In one embodiment of the apparatus according to the invention, at least one recess is designed and provided in the sleeve such that at least three different openings or outlets can be formed by superposing the shaft aperture and the sleeve aperture (e.g. by shifting or moving the sleeve inside the shaft or the shaft inside the sleeve).

Whenever it is herein referred to "at least three different openings", these openings can each have a different geometrical shape, according to one embodiment of the present invention. In other words, the openings can differ in their design.

In one embodiment of the present invention, the "three different openings" can differ in the size of their respective area.

In one embodiment of the present invention, such an opening is defined as the open passage between an exterior of the apparatus or of the shaft of the apparatus and an interior of the apparatus or of the shaft.

In one embodiment of the present invention, such an opening is an area in which a passage both through the shaft aperture (i.e. an opening in the wall of the shaft) and through the sleeve aperture (i.e. an opening in the wall of the sleeve) is open in the sense of a passage opening.

In one embodiment of the present invention, the "three different openings" can differ in their function.

For example, in one embodiment of the present invention, a first opening can be large enough to allow introducing one or several tension threads from an exterior of the apparatus into an interior of the apparatus, e.g., both through a wide area of the sleeve aperture and a shaft aperture adjoining or neighboring the latter.

In one embodiment of the present invention, a second opening can have the function (and the shape required thereto) not to be large enough for allowing (preferably easy) introduction of a tension thread through a wide area of the sleeve aperture. The wide area of the sleeve aperture can thus, for example, be covered by the shaft wall. The second opening can have the function to lead at least two tension threads through at least two recesses in such a way that the tension threads cannot touch each other and/or cannot get in contact with each other in the recesses and/or cannot entangle themselves.

In one embodiment of the present invention, a second opening can have the function of not bringing a separation device or a cutting device in contact with one or all of the tension threads or of inhibiting such a contact.

In one embodiment of the invention, the separation device or the cutting device can be covered at the second opening by a portion of the wall such that the tension threads cannot get in contact with the separation device or the cutting device.

In one embodiment of the invention, the openings can each comprise a range of geometrical shapes. Therefore, the openings need not to have an unchangeable shape or size as long as the respective function (and optionally this function alone) is possible in the respective range of the geometrical shape. However, each opening can be variable within the limits given by the corresponding range.

In one embodiment of the invention, the apparatus is designed for folding and/or unfolding an implant in form of a stent or a cardiac valve assembly.

The object of the present invention is also solved by the set according to the invention. The set according to the invention includes at least one apparatus according to the invention and at least one implant connected to tension threads for the purpose of its folding and/or unfolding.

In one embodiment of the set according to the invention, the implant is a foldable and/or unfoldable implant.

Furthermore, the object of the invention is solved by the method according to the invention. The method according to the invention comprises using an apparatus according to the invention or a set according to the invention.

In one embodiment of the method according to the invention, the method comprises altering the tension that is exerted on an implant by using at least one tension thread. The tension is preferably controlled by altering a length of the pulling device branching off the interior of the shaft.

In one embodiment of the method of the present invention, the method further comprises cutting or cutting through, respectively, at least one tension thread by inducing, enabling or allowing a relative movement between the shaft and the sleeve.

The advantages achievable by the apparatus according to the invention can also be achieved by the set according to the invention and by the method according to the invention.

Among the advantages achievable according to the present invention is the possibility of independently actuating tension threads. This is due to the self balancing design. Thus, it is possible to specifically fold and/or unfold implants having a plurality of tension threads. Parts or sections of the implant can thus be folded or unfolded though other parts or sections of the implant have already been completely folded or unfolded. This can i.a. be reasonable when an unfolded implant and the implantation site do not completely match in their dimensions, or if the implant does, e.g., not have a uniform shape over its entire length.

Furthermore, the possibility of simply connecting tension threads to the apparatus, for example, by means of and trough the wide area of the sleeve aperture in one embodiment of the invention, is one of the advantages achievable according to the present invention.

Another advantage is that the tension threads can in one embodiment of the present invention be led or guided separately from each other. A mutual interference of the tension threads can thus be avoided.

In one embodiment of the present invention, it is advantageously possible to separate at least one tension thread from the implant. The thread can particularly be cut through by means of a cutting device.

Another advantage arises from the fact that, in one embodiment according to the invention, only one tension thread (or two or more threads) can specifically be separated or detached or cut through, while other tension threads will not be separated, detached or cut through. Particularly for a sloop-like or loop-like design of the tension threads, it is thus possible to cut through a portion of the tension thread instead of the sloop as a whole. In that way, the whole material that had constitute the sloop or loop can be retracted into the shaft by pulling the non-cut parts or side of the sloop of the tension thread(s). In other words, the tension threads not cut through can be used for separating or detaching all tension threads from the implant by simply pulling the tension thread. This can advantageously be useful i.a. after an implantation.

In the following, an example of the present invention will be described with reference to the accompanying drawing. On the drawing, similar or identical assemblies or elements are denoted by the same reference numbers.

FIG. 3 shows schematically simplified and in part section, a set according to the invention with an implant expanding though the action of the apparatus according to the invention;

FIG. 4 shows the set of FIG. 3 with the implant in a further (partly) folded condition by means of the apparatus according to the invention;

Figure 1:
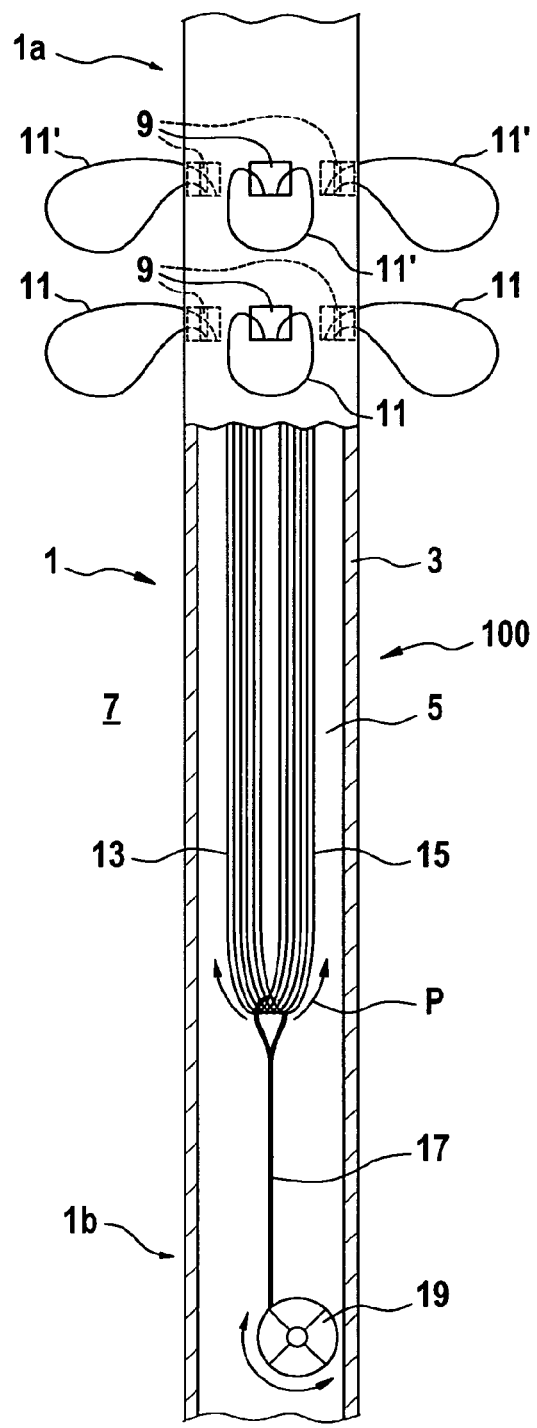
FIG. 1 shows a longitudinal part section through a schematically simplified cutaway view of the apparatus according to the invention.

FIG. 1 shows a part longitudinal section through a part-sectioned, schematically simplified view of the apparatus 100 according to the invention. The apparatus 100 has a shaft 1 with wall 3. Shaft 1 is in the upper area 1a of FIG. 1 shown not sectioned and in the lower area 1b longitudinally sectioned in such a way that an open view of the interior 5 of shaft 1 is possible.

The wall 3 separates the interior 5 of shaft 1 from an exterior 7 of shaft 1, the exterior 7 of shaft 1 can be an outer part of apparatus 100 (so an external layer). The shaft 1 can however still be surrounded by a further structure (not shown in FIG. 1).

Shaft 1 features apertures 9. In FIG. 1, 6 such shaft apertures 9 are shown. This quantity is purely an example to assist explanation.

The shaft apertures 9 can thereby be evenly spaced from each other around the circumference of shaft 1. They can be divided with at least 2 different distances from each other around the circumference.

The shaft apertures 9 can as shown in FIG. 1 pass through the total thickness of wall 3 of shaft 1 so be developed as connecting openings.

Through the shaft apertures, a tension thread or several tension threads 11 and 11' can be threaded from the interior 5 of shaft 1 to the exterior 7 of shaft 1 and/or threaded-in from the opposite direction. In FIG. 1 all the threads 11 and 11' pass both in and out of the shaft apertures 9 in loop-form.

The threads 11 and 11' are arranged to hold an implant not shown in FIG. 1 so that the implant diameter can be altered through varied tension in the threads 11 and 11'.

Figure 2:
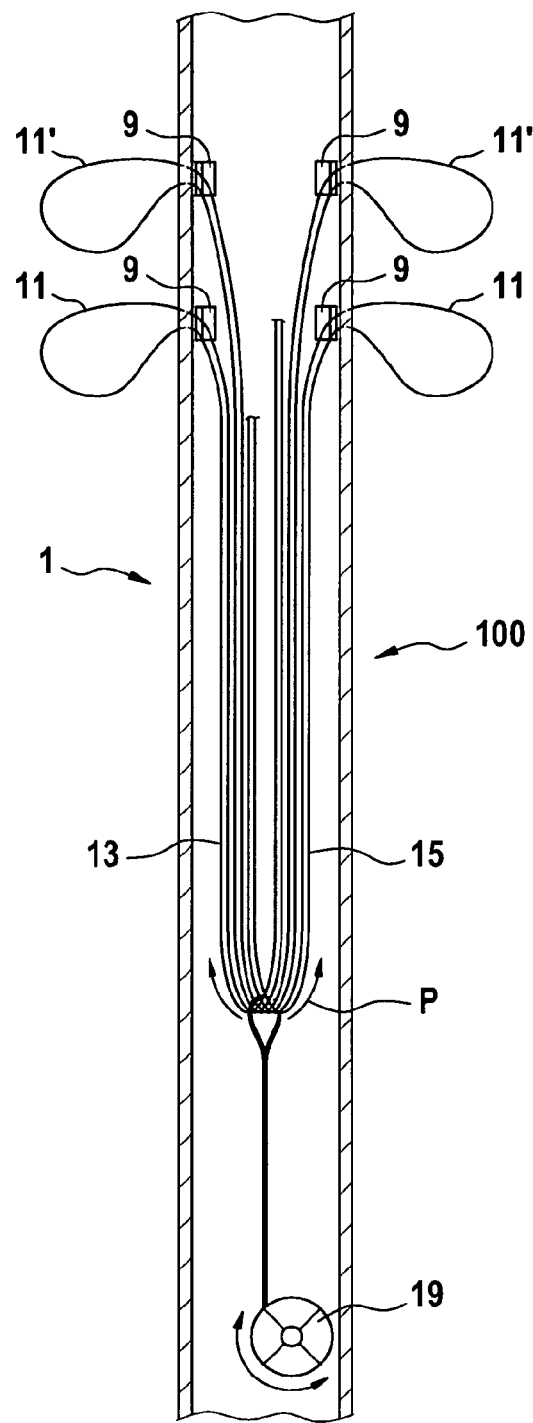
FIG. 2 shows the object in FIG. 1 in a full longitudinal section.

As can from the sectioned lower area 1b of the shaft 1 in FIG. 1 be understood and with reference to FIG. 2 becomes clearer, a number of threads 11' are collected together to a first bundle 13 and the other threads 11 to bundle 15. In the bundle, the threads can be provided to be effected or pulled separately from each other.

In FIG. 1 as an example the upper three threads 11' are grouped together in bundle 13 while the lower three threads 11 are grouped together in a second bundle 15. This arrangement is purely for example and can be defined in any other order.

In a lower area of shaft 1, bundles 13 and 15 are joined together.

In a lower area of shaft 1, a pulling thread 17 loops over bundles 13 and 15 for being engaged with them such as to be capable to transmit a pulling force on threads 13 and 15.

By virtue of the sliding connection of bundles 13 and 15 to pulling thread 17, force in the direction of the lower area of FIG. 1, can bring to bear tension or force on bundle 13 or bundle 15. Thereby can increased tension be brought to bear on bundle 13 when tension on bundle 15 can be allowed to increase no further (or reduce of course). Likewise the tension on the first bundle 13 can be reduced when the pulling thread 17 is brought back in the direction of upper end of FIG. 1, also when by means of the pulling thread 17 no more tension can be brought to bear on (or reduced from the second bundle 15. That is, usually force or tension on bundle 13 and bundle 15 are the same at each particular point of time. It is always the same force on both bundle 13 and 15, only when there is less resistance on one side, this side will elongate, until forces become the same again. The same situation applies during pulling. Even when bundle 13 and bundle 15 have different lengths, or different pulling distance, the force and tension should be always balanced, i.e. the same on both sides.

This effect of independently operated bundles (here bundles 13 and 15) together with the invention here presented will be designated as "self balancing design". It is achievable through the special connection of bundles 13 and 15 with the pulling thread 17 with a free through movement of bundles 13 and 15 which is enabled by the loop design of pulling thread 17. This connection allows a sliding movement of bundles 13 and 15 through the loop of the pulling thread 17 in both the directions indicated by arrow P.

The tension of the pulling thread 17 is in turn adjustable by means of a rotation or tensioning device.

It is clear that this "self balancing design" is not limited to two bundles which can moreover be developed as single threads and not to a further thread—here the pulling thread 17.

Tension or pull exerted by means of the pulling thread 17 will be carried through to the threads 11 and 11' by means of bundles 13 and 15. In this manner an operation of the pulling thread 17 can bring about a change in one or more cross-section dimensions of the implant not shown in FIG. 1.

FIG. 2 shows the object in FIG. 1. In FIG. 2 shaft 1 is actually sectioned or cut open over the complete length shown. There is no difference shown between the two areas 1a and 1b, Hence in FIG. 2 only 4 of the 6 thread loops 11 and 11' indicated in FIG. 1 are shown.

FIG. 2 is to illustrate how the bundles 13 and 15 of tensioning threads being separately provided from each other devolve into threads 11 and 11' with respect to the grouping together of the latter in the bundles 13 and 15.

Figure 2A:
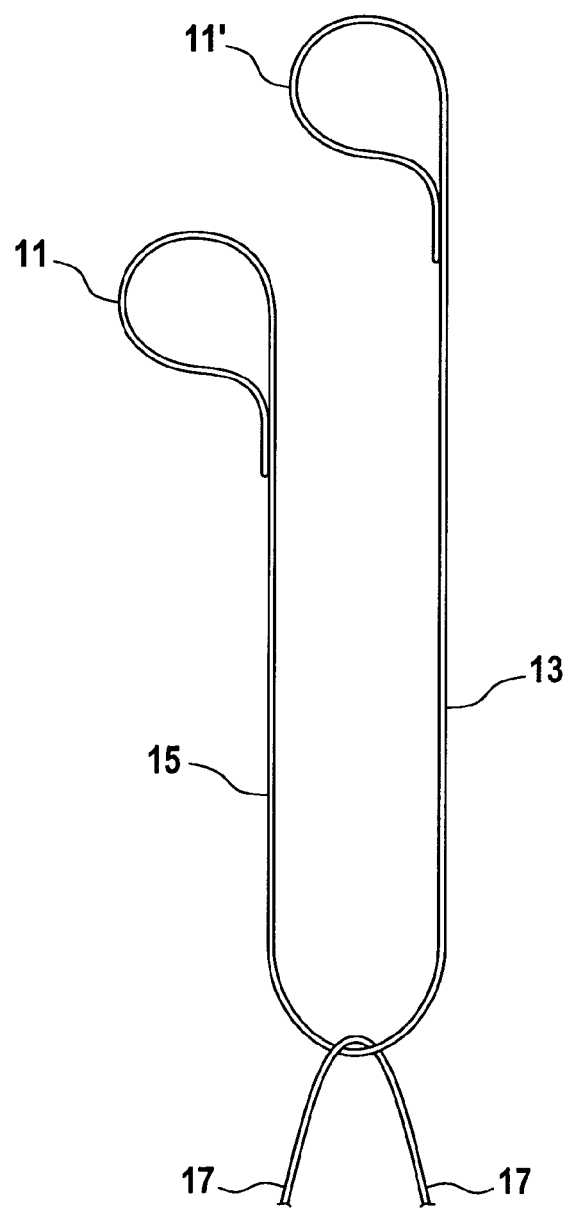
FIG. 2A shows the self-balancing design shown in FIG. 1 and FIG. 2 in a schematically simplified manner.

FIG. 2A shows the self-balancing design shown in FIGS. 1 and 2 in a schematically simplified manner for only one bundle 13/15, ending with two loops 11 and 11', respectively. It is obvious from FIGS. 1, 2 and 2A that each loop of tensioning threads 11' enters the shaft 1 through a first aperture 9 for joining the downwards directed bundle 13, passing through the tensioning thread 17 for going up again as a part of bundle 13 so as to go out through a second aperture 9 (being arranged below the first aperture 9). That is, each tensioning thread 11 surrounding a portion of the stent (implant) near the base thereof is integrally formed with one tensioning thread 11', with the tensioning thread 11' surrounding a portion of the stent (implant) near the tip thereof.

FIG. 3 shows a set 200 according to the invention with an implant 300 expanding through an apparatus 100 according to the invention. The expansion can benefit in the present through the internal stress of implant 300. An implant of this specification can expand itself although only after a corresponding release of the pulling thread 17.

As to be seen in FIG. 3 (and likewise in FIG. 4) set 200 is shown only with one upper thread 11' and one lower thread 11. This reduction (simplification) is used for improved clarity. It is therefore clear that any arbitrary number of upper and lower threads 11 and 11' can be provided.

FIG. 4 shows a set 200 according to the invention from FIG. 3 with an implant 300 by means of apparatus 100 according to the invention in a partly folded condition, through the further folding of the implant (in comparison with the condition in FIG. 3) the pulling threads 17 protrudes further out of shaft 1 in the direction of lower part of the view as in FIG. 4.

Figure 5:
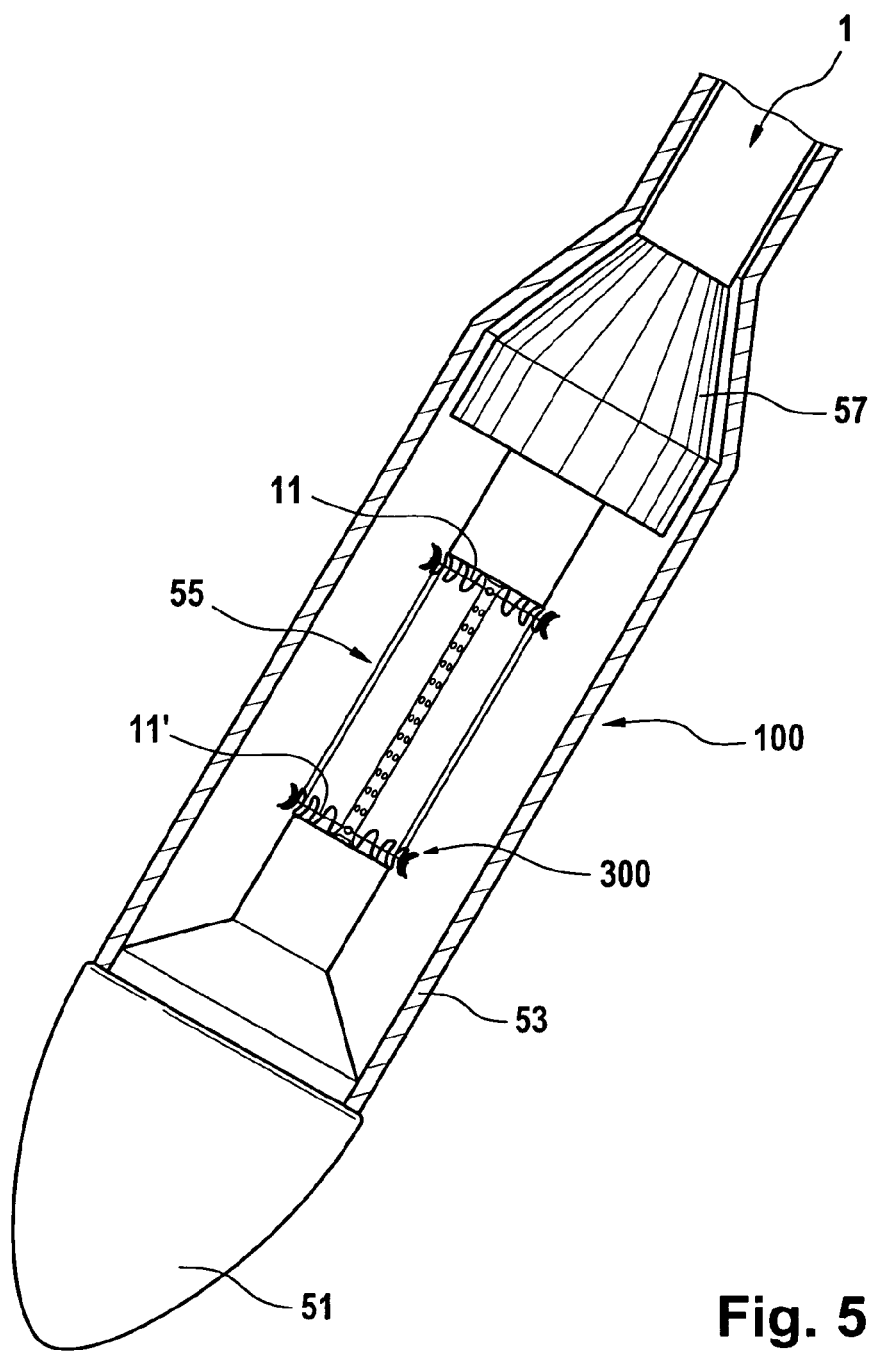
FIG. 5 shows the tip of an apparatus according to the invention shown in a closed condition prior to implantation.

FIG. 5 shows in part section the tip 51 of an apparatus 100 according to the invention shown in a closed condition prior to implantation.

Shown in part section is an exterior protective sleeve which gives protection to a retaining area 55 for the implant 300, in this case a stent which is stored between the tip 51 and a collar 57. The collar 57 may advantageously guide the sleeve over the implant 300, e.g. when being a crimped stent.

The implant 300 is held in a restrained state in which the implant 300 is not expanded, by means of the threads 11 and 11'.

Figure 6:
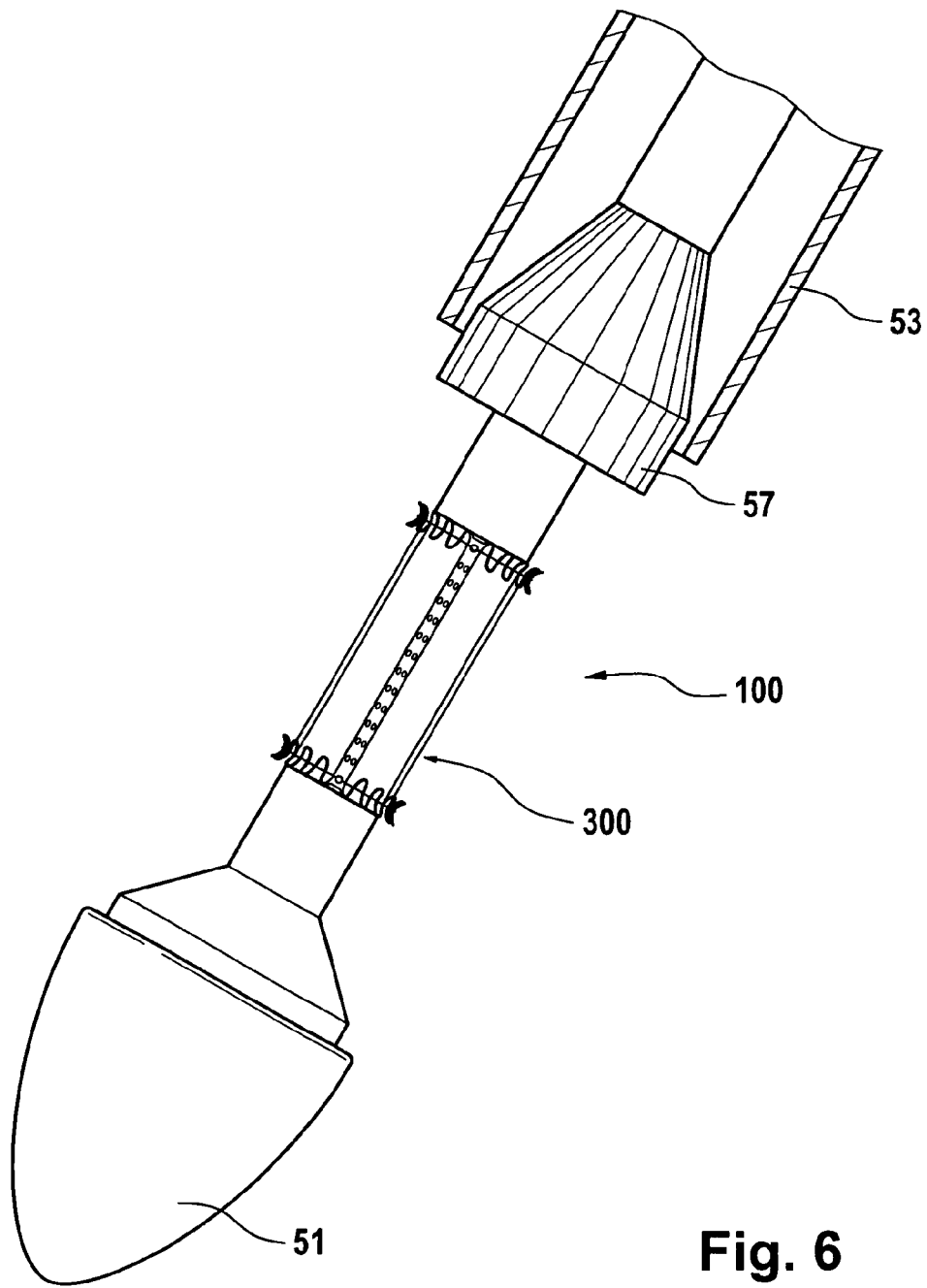
FIG. 6 shows the tip of the apparatus according to the invention as in FIG. 5 prior to implantation with partially withdrawn outer sleeve.

FIG. 6 shows the tip 51 of an apparatus 100 according to the invention in FIG. 5 prior to implantation, with a partly withdrawn external protective sleeve 53. Through the withdrawal of the outer protective sleeve the implant is released for implantation. The restrained state is substantially or fully maintained through the tension of the circumferential threads 11 and 11'.

Figure 7:
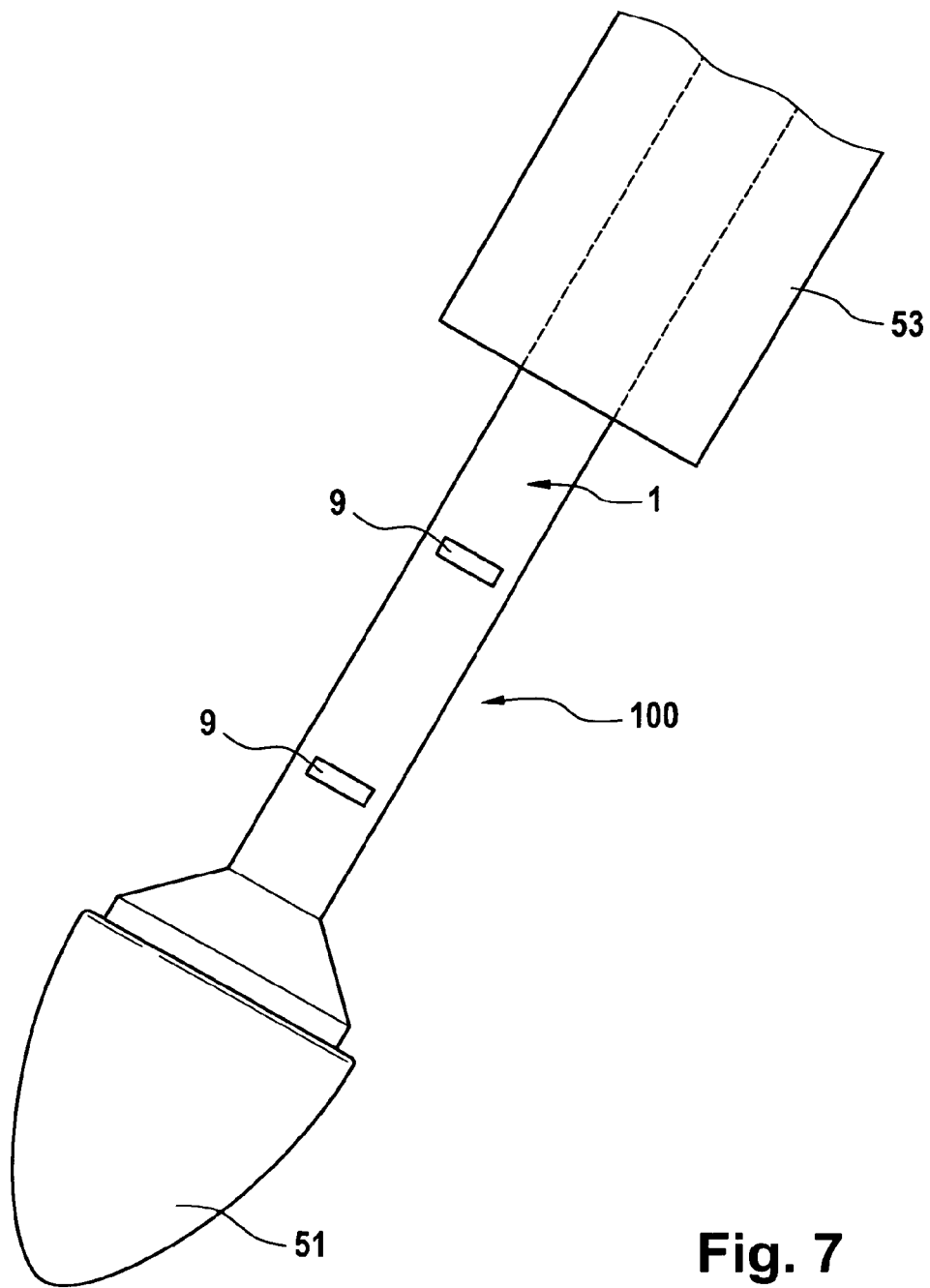
FIG. 7 shows the tip of an apparatus according to the invention as in FIG. 6 without implant.

FIG. 7 shows the tip 51 of an apparatus 100 according to the invention of FIG. 6 without implant, to be noted now are the shaft apertures 9 through which the threads 11 and 11' not shown in FIG. 7 (see FIGS. 5 & 6) exit and enter shaft 1.

Figure 8:
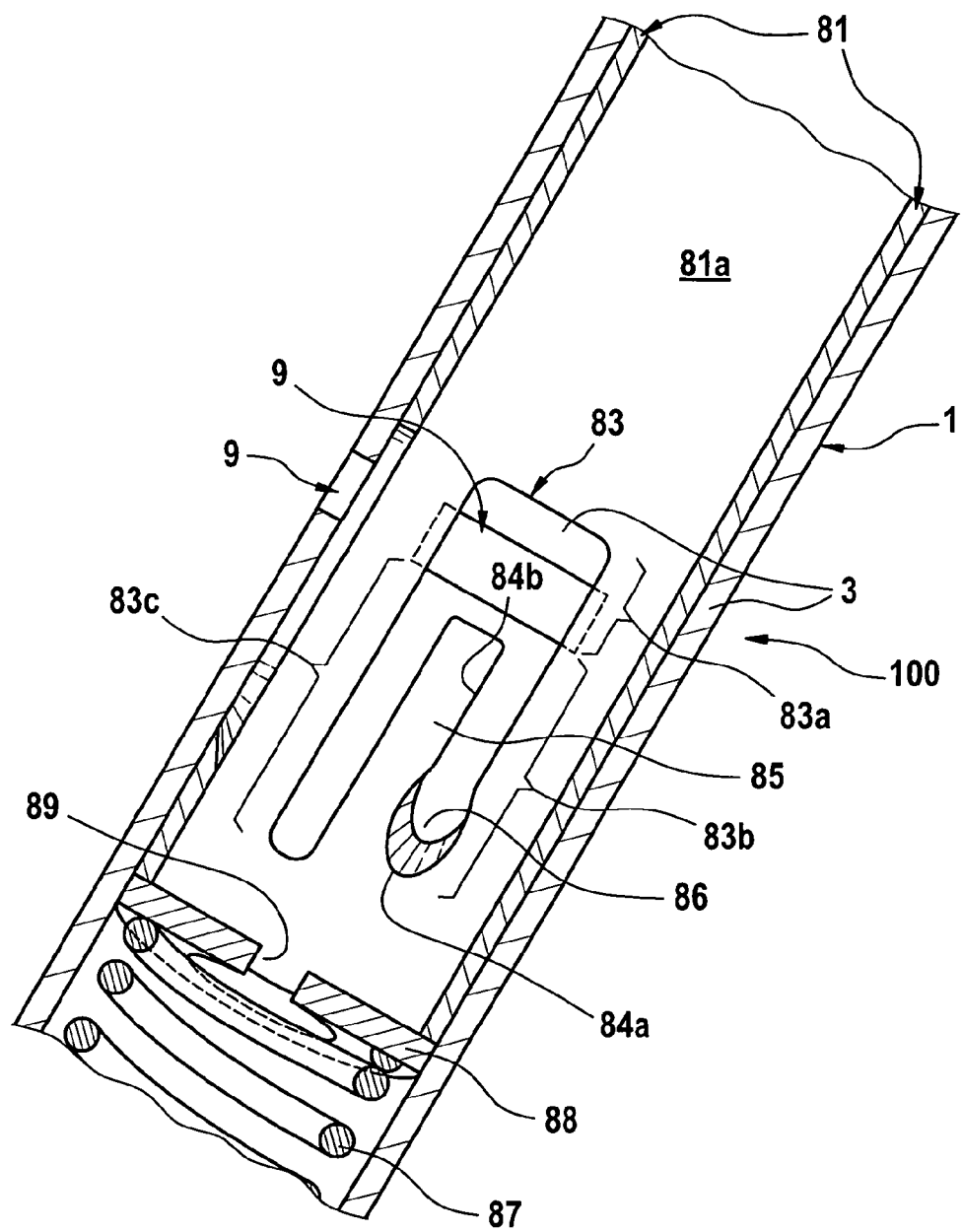
FIG. 8 shows the shaft and the sleeve of the apparatus according to the invention of FIG. 6 in part view, in a part section and with a first opening.

FIG. 8 shows the shaft 1 and herein arranged movable sleeve 81 of an apparatus 100 according to the invention of FIG. 6, in a part sectioned part view in the first position of sleeve 81 on shaft 1.

The sleeve 81 features an opening 83 of the sleeve 81 comprising a wide area 83a, a first recess 83b and a second recess 83c. The first recess 83b and the second recess 83c are separated from one another by a bar 85.

Recesses 83b and 83c can be of different lengths as shown in FIG. 8. They can alternatively have different lengths in another spatial envelope.

Bar 85 is able to separate two threads from one another, one of which runs through the first recess 83b and the second runs through the second recess 83c.

As can be seen in FIG. 8, located on the recess 83b and/or on the bar 85 on the side facing the recess 83b or 83c may optionally be an initial area 84a with a cutting device 86. Located on the recess and on bar 85 on the side facing the recess 83b and/or the recess 83c may optionally be a second area 84b without a cutting device.

In the first position the threads (not shown in FIG. 8) can be threaded from the outside of shaft 1 through the shaft aperture 9 and the wide area 83a of sleeve 81 into the inside of sleeve 81.

This first position is suitable for the insertion of the threads into apparatus 100. This position can be achieved by bringing a pre-tensioning device 87 under an increased tension. The pre-tensioning device is by way of example shown as a spring, or more precisely a coil spring.

Further there is a sealing device 88 with an opening 89 for a guide wire that is not shown in this view.

A second shaft aperture 9 with a second sleeve aperture 83 is shown by a cutaway section on the outer sleeve of shaft 1 on the left side. By means of this through section an otherwise obscured view through shaft 1 and sleeve 81 of the inside shaft 1 is made possible.

Figure 9:
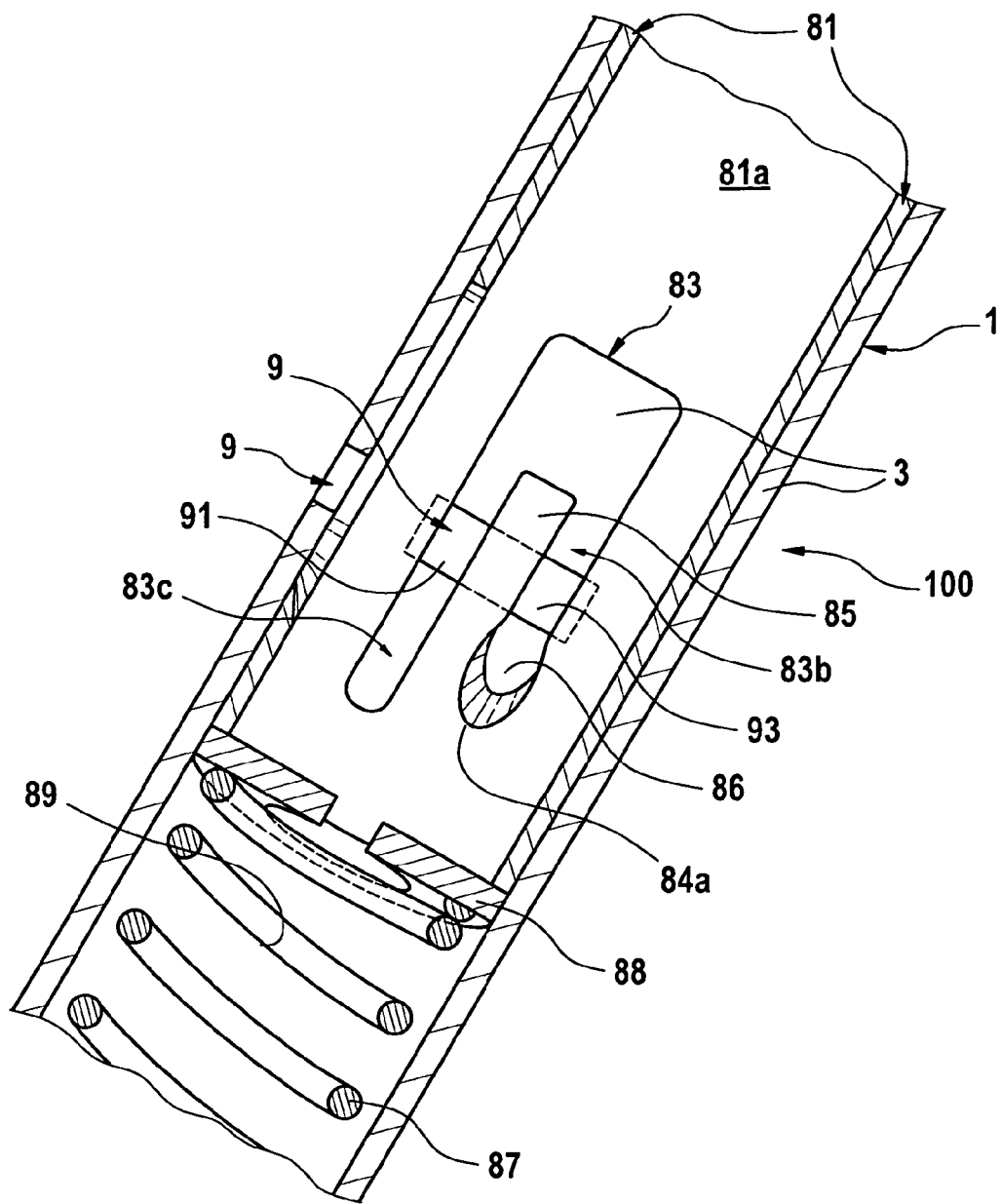
FIG. 9 shows the shaft and the sleeve of the apparatus according to the invention of FIG. 6 in part view, in a part section and with a second opening.

FIG. 9 shows the arrangement as in FIG. 8 in a second position.

In the second position the load in the pre-tensioning device 87 is reduced from that in FIG. 8. It is clearly no longer under load in FIG. 9. In FIG. 9 the sleeve 81 is slid further up to the right (ref FIG. 9). This also applies to the sleeve apertures 83. The bar 85 thereby divides the shaft apertures to the extent that the shaft aperture 9 with sleeve aperture 83 now give a passage from the outside of shaft 1 to the inside sleeve 83 through two shaft part apertures 91 and 93. It is possible, pertaining to the invention, that the transition from the first to the second position may be brought about solely or with the assistance of the pre-tensioning device or indeed the be brought about manually.

In the second position are two threads (not shown in FIG. 9) one of which is for example passed through the shaft part aperture 91 and the other passed through shaft part aperture 93 separated from one another by bar 85. This division can be advantageous in forestalling a tangling or functional obstruction of the two threads, or in the area of the shaft apertures at least reduce these. Lastly, it is advantageous chiefly if the threads are to be operated separately from one another.

Figure 10:
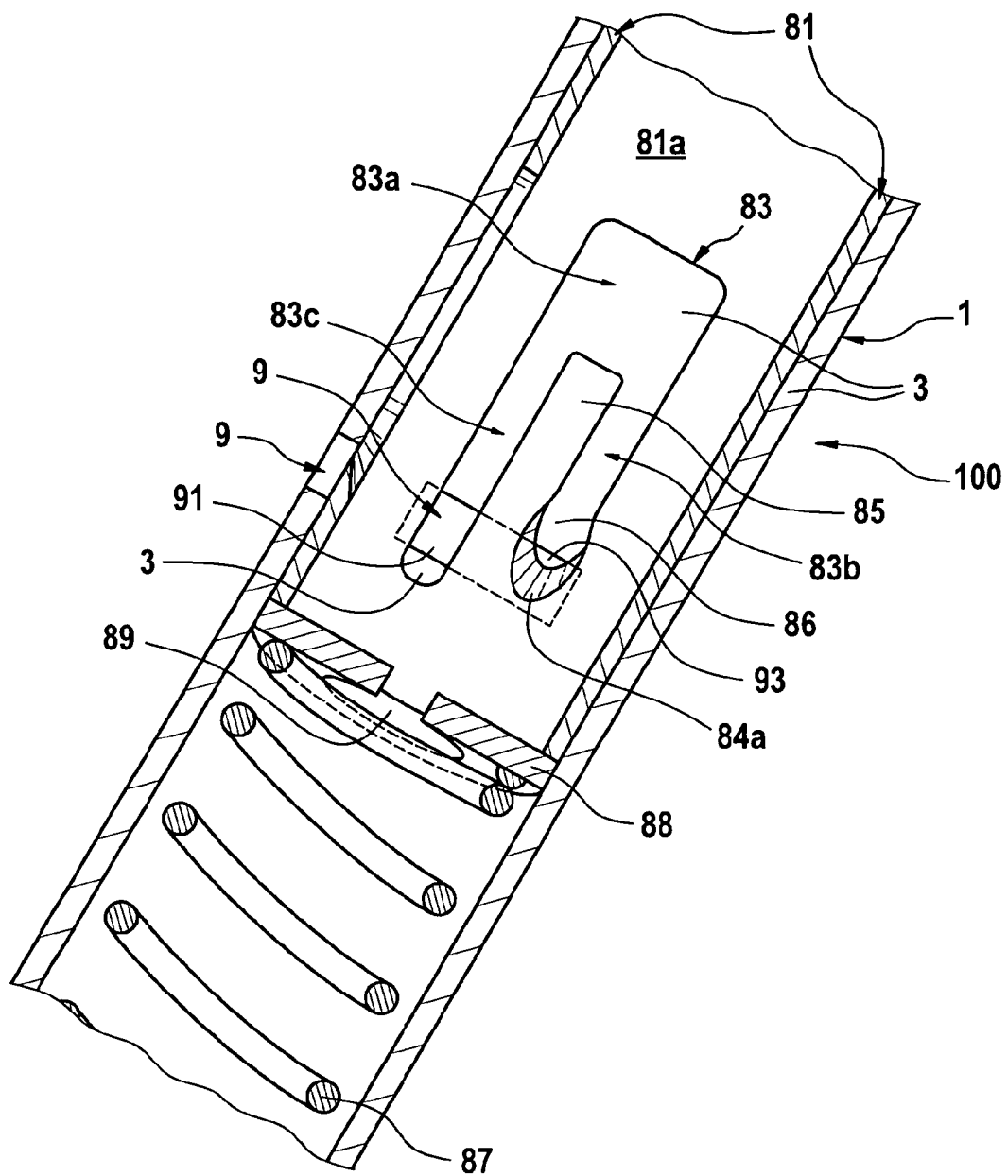
FIG. 10 shows a shaft and sleeve of the apparatus according to the invention of FIG. 6 in part view, in a part section and in a third opening.

FIG. 10 shows the arrangements of FIG. 8 and FIG. 9 in a third position.

In the third position the shaft part aperture is further reduced to such an extent that a thread (not shown) which is running through the shaft part aperture 93 comes into contact with the cutting device in the second area 84b.

By sliding the sleeve 81 further up to the right (in FIG. 10) relative to shaft 1, further towards the nearer end of shaft 1, the shaft part aperture will become smaller and the thread (not shown) finally cut through. This position which is continued on from the third position is shown in FIG. 11.

Figure 11:
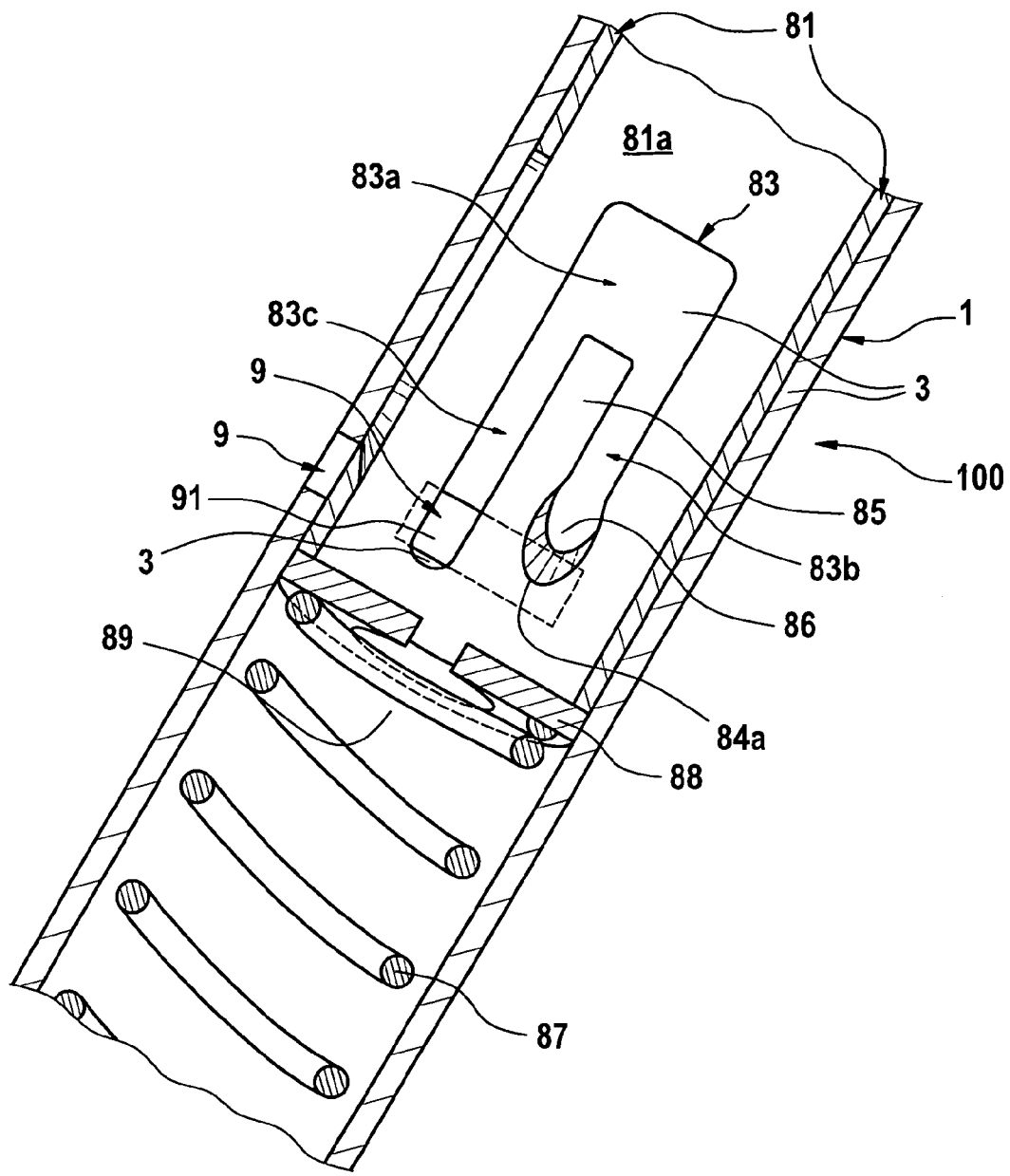
FIG. 11 shows a shaft and sleeve of the apparatus according to the invention of FIG. 6 in part view, in a part section after passing through the third opening.

In FIG. 11 it can be seen that the shaft part aperture 93 no longer exists. The shaft part aperture 91 of FIGS. 9 and 10 is closed by the wall 3 of shaft. The thread is completely severed.

The invention claimed is:

1. An apparatus (100) for folding or unfolding at least one medical implant (300) by using tension threads (11, 11'), wherein the apparatus (100) comprises:
    a shaft (1) comprising a reception area for receiving the implant (300), wherein the shaft comprises at least two lateral shaft apertures (9) on different planes of the shaft through which the tension threads can be led between an interior of the shaft and an exterior of the shaft and wherein the threads are led within an interior of the shaft in a longitudinal direction thereof;
    a tensioning device (19) for altering a shape of the implant (300) via the tension threads (11, 11'), wherein the tensioning device (19) comprises at least one pulling device which is arranged to apply tension on the implant (300) via the tension threads (11, 11') to alter the shape of the implant (300), and to reduce the tension applied on the implant (300) from the tension threads (11, 11'); and
    a separation device for separating the tension threads (11, 11') from the implant (300), wherein the separation device comprises a cutting device (86) for cutting through the tension threads (11, 11'), wherein the separation device is part of a sleeve aperture (83) in a wall of a sleeve (81) of the apparatus (100), the sleeve aperture (83) comprising a first recess (83b), in which a first tension thread is guided during use, and a second recess (83c), in which a second tension thread is guided during use, wherein the first recess (83b) and the second recess (83c) are separated by a bar (85) to space the first tension thread and the second tension thread apart from each other and wherein the separation device is disposed within the shaft and is configured to be slidable relative to the shaft (1).

2. An apparatus (100) according to claim 1, wherein the pulling device is arranged and/or provided for interacting with the tension threads (11, 11') in order to transfer force or tension, wherein the pulling device and the tension threads (11, 11') are intricate with each other.

3. An apparatus (100) according to claim 1, wherein the pulling device comprises at least one pulling thread (17).

4. An apparatus (100) according to claim 3, wherein the tension threads (11, 11') and/or the at least one pulling thread (17) constitute a bundle or a plurality of threads or thread elements.

5. An apparatus (100) according to claim 1, wherein the sleeve aperture (83) connects an exterior of the sleeve (81) with an interior of the sleeve (81).

6. An apparatus (100) according to claim 5, wherein the interior of the shaft (1) is permeable or can be passed in at least sections thereof in a longitudinal direction of the shaft (1), wherein the shaft (1) has a wall (3), and wherein tension threads (11, 11') for folding and/or unfolding the implant (300) can enter and/or leave one of the at least two shaft apertures, and wherein the sleeve (81) is arranged in the interior (5) or in the exterior (7) of the shaft (1) of the apparatus (100) in a state of use of the apparatus (100) such that tension threads (11, 11') can be led through both the shaft (1) and the sleeve (81) from the exterior of the apparatus (100) into an interior of the apparatus (100).

7. An apparatus (100) according to claim 6, wherein recesses (83b, 83c) are arranged in the sleeve (81) such that at least three different openings between an exterior (7) of the shaft (1) and the interior (82) of the sleeve (81) can be established by superposing one of the at least two shaft apertures (9) and the sleeve aperture (83).

8. An apparatus (100) according to claim 5, comprising a pre-tensioning device (87) which is arranged for exerting tension onto the sleeve (81) in at least one state of use.

9. An apparatus (100) according to claim 1, wherein the first recess (83b) comprises a portion (84b) without a cutting device.

10. An apparatus (100) according to claim 1, wherein the first recess (83b) has a first extension in a dimension of the apparatus (100) which differs from a second extension of the second recess (83c) in a same dimension of the apparatus (100).

11. An apparatus (100) according to claim 1, wherein the implant (300) is a stent or a cardiac valve assembly.

12. A set comprising at least one apparatus (100) according to claim 1; and
    at least one implant (300) connected with tension threads (11, 11') for the purpose of being folded and/or unfolded.

13. A method comprising:
using an apparatus (100) according to claim 1 to fold or unfold at least one medical implant (300) by using the tension threads.

14. A method according to claim 13, further comprising:
altering a tension having been applied on the implant (300) via tension threads (11, 11') by altering a length of a pulling device branching off the interior (5) of the shaft (1).

15. A method according to claim 13, further comprising:
cutting through tension threads (11, 11') via the separation device by inducing, enabling or allowing a relative movement between the shaft (1) and a sleeve (81).

* * * * *